(12) United States Patent
Bielawa et al.

(10) Patent No.: US 11,826,142 B2
(45) Date of Patent: *Nov. 28, 2023

(54) APPARATUS AND METHOD FOR TAKING BLOOD GLUCOSE MEASUREMENTS AND RECOMMENDING INSULIN DOSES

(71) Applicant: Hygieia, Inc., Livonia, MI (US)

(72) Inventors: Holly Bielawa, Ann Arbor, MI (US); Carissa Demetris, Ann Arbor, MI (US); James Goebel, Ypsilanti, MI (US); Carol Treat Morton, Bloomfield Township, MI (US); Michelle Pomorski, Pinckney, MI (US); Thomas Puricelli, Ann Arbor, MI (US); Jim Rogers, Ann Arbor, MI (US); Eran Bashan, Ann Arbor, MI (US); Israel Hodish, Ann Arbor, MI (US); John Hindinger, Farmington Hills, MI (US)

(73) Assignee: Hygieia, Inc., Livonia, MI (US)

( * ) Notice: Subject to any disclaimer, the term of this patent is extended or adjusted under 35 U.S.C. 154(b) by 383 days.

This patent is subject to a terminal disclaimer.

(21) Appl. No.: 16/863,027

(22) Filed: Apr. 30, 2020

(65) Prior Publication Data

US 2020/0402655 A1     Dec. 24, 2020

Related U.S. Application Data

(63) Continuation of application No. 15/947,448, filed on Apr. 6, 2018, now Pat. No. 10,679,747, which is a
(Continued)

(51) Int. Cl.
A61B 5/145  (2006.01)
A61B 5/00  (2006.01)
(Continued)

(52) U.S. Cl.
CPC ........ *A61B 5/14532* (2013.01); *A61B 5/4839* (2013.01); *A61M 5/1684* (2013.01);
(Continued)

(58) Field of Classification Search
None
See application file for complete search history.

(56) References Cited

U.S. PATENT DOCUMENTS 4,731,726 A * 3/1988 Allen, III ........... A61B 5/14532
128/920
5,053,199 A * 10/1991 Keiser .................... G06K 7/006
439/70
(Continued)

FOREIGN PATENT DOCUMENTS

WO    WO 2006/072035    7/2006

OTHER PUBLICATIONS

International Search Report dated Jan. 11, 2011 for PCT/US2010/055246.

*Primary Examiner* — Matthew D Krcha
*Assistant Examiner* — Brittany I Fisher
(74) *Attorney, Agent, or Firm* — Jones Day

(57) ABSTRACT

The present disclosure related to an apparatus that may be used for taking blood glucose measurements and providing individualized insulin dose recommendations wherein the apparatus is easy to use and facilitates improved diabetes control in patients. Also disclosed are related methods.

16 Claims, 14 Drawing Sheets

Related U.S. Application Data continuation of application No. 15/094,634, filed on Apr. 8, 2016, now Pat. No. 10,007,760, which is a continuation of application No. 12/926,234, filed on Nov. 3, 2010, now Pat. No. 9,341,614.

(60) Provisional application No. 61/257,886, filed on Nov. 4, 2009.

(51) Int. Cl.

| | | |
|---|---|---|
| *A61M 5/168* | (2006.01) | |
| *A61M 5/172* | (2006.01) | |
| *G01N 33/487* | (2006.01) | |
| *G16H 10/40* | (2018.01) | |
| *G16H 20/10* | (2018.01) | |
| *G01N 27/327* | (2006.01) | |
| *G16H 20/17* | (2018.01) | |
| *G16H 20/60* | (2018.01) | |
| *G16H 40/63* | (2018.01) | |
| *A61M 5/315* | (2006.01) | |
| *A61M 5/142* | (2006.01) | |
| *G01N 21/84* | (2006.01) | |

(52) U.S. Cl.
CPC ..... *A61M 5/1723* (2013.01); *G01N 33/48792* (2013.01); *G16H 10/40* (2018.01); *G16H 20/10* (2018.01); *G16H 20/17* (2018.01); *G16H 20/60* (2018.01); *G16H 40/63* (2018.01); *A61M 5/31571* (2013.01); *A61M 2005/14208* (2013.01); *A61M 2205/502* (2013.01); *A61M 2205/507* (2013.01); *A61M 2205/52* (2013.01); *G01N 21/8483* (2013.01); *G01N 27/3271* (2013.01); *G01N 27/3273* (2013.01)

(56) References Cited

U.S. PATENT DOCUMENTS

| | | |
|---|---|---|
| 7,570,980 B2 | 8/2009 | Ginsberg |
| 8,282,578 B2 | 10/2012 | Rush et al. |
| 2002/0054827 A1 | 5/2002 | Patel et al. |
| 2004/0048394 A1* | 3/2004 | Kirchhevel ............ G07F 11/54 436/95 |
| 2004/0199409 A1 | 10/2004 | Brown |
| 2005/0192494 A1 | 9/2005 | Ginsberg |
| 2005/0277164 A1* | 12/2005 | Drucker ................. A61B 5/743 435/14 |
| 2006/0233666 A1 | 10/2006 | Vu et al. |
| 2008/0262469 A1 | 10/2008 | Brister |
| 2008/0294024 A1 | 11/2008 | Cosentino et al. |
| 2008/0300572 A1* | 12/2008 | Rankers ............ A61B 5/14532 604/504 |
| 2009/0105570 A1 | 4/2009 | Sloan et al. |
| 2009/0253970 A1 | 10/2009 | Bashan et al. |
| 2009/0253973 A1 | 10/2009 | Bashan et al. |
| 2010/0286563 A1 | 11/2010 | Bryer |
| 2011/0148905 A1 | 6/2011 | Simmons |

\* cited by examiner

```
        R
Medication  Summary  Setting
      Novolog Mix 70/30
      Breakfast - 72 Units
      Dinner - 32 Units
12-07                  12:05PM
```

FIG. - 12

```
Glucose  Event  Dose  Summary
         72 units
       Novolog Mix 70/30
12-07                   7:05AM
```

FIG. - 13

```
Glucose  Event  Dose  Summary
         17 units
           Novolog
12-07                   7:05AM
```

FIG. - 14

| Glucose | Event | Dose | Summary |

36 units
Lantus 12-07                                    10:05PM

FIG. - 15

| ℞ Medication | Summary | Setting |

Novolog
Breakfast  11   Lunch  13
   Dinner  12   CF    1:30
12-07                        12:05PM

FIG. - 16

| Glucose | Event | Carbs | Dose |

065 grams

| Glucose | Event | Carbs | Dose |
|---------|-------|-------|------|
| | 19 units Novolog | | |
| 12-07 | | | 12:05PM |

FIG. - 18

```
┌─────────────────────────────────────┐
│              ѰӀ                     │
│ Glucose   Event   Carbs    Dose     │
├─────────────────────────────────────┤
│                                     │
│      Low Glucose                    │
│                                     │
│ 12-07                       12:05PM │
└─────────────────────────────────────┘
```

FIG. 22

```
┌─────────────────────────────────────┐
│                           🗐         │
│ Event   Carbs    Dose   Summary     │
├─────────────────────────────────────┤
│ ▆▬▸ 42 mg/dL      ѰӀ Lunch          │
│         Low Glucose                 │
│ 12-07                       12:05PM │
└─────────────────────────────────────┘
```

APPARATUS AND METHOD FOR TAKING BLOOD GLUCOSE MEASUREMENTS AND RECOMMENDING INSULIN DOSES

CROSS REFERENCE TO RELATED APPLICATIONS

This application is a continuation of U.S. application Ser. No. 15/947,448 filed Apr. 6, 2018, which is a continuation of U.S. application Ser. No. 15/094,634, filed Apr. 8, 2016, now U.S. Pat. No. 10,007,760, issued Jun. 26, 2018, which is a continuation of U.S. application Ser. No. 12/926,234, filed Nov. 3, 2010, now U.S. Pat. No. 9,341,614, issued May 17, 2016, which claims the benefit of U.S. Provisional Application 61/257,886, filed Nov. 4, 2009. The entire contents of each of the foregoing applications is incorporated herein by reference in their entirety.

U.S. Design Pat. No. D622,394 issued on Aug. 24, 2010, U.S. Provisional Application No. 61/042,487, filed Apr. 4, 2008, U.S. Provisional Application No. 61/060,645, filed Jun. 11, 2008, U.S. Provisional Application No. 61/113,252 filed Nov. 11, 2008, International Applications PCT/US2009/039421, filed Apr. 3, 2009, PCT/US2009/039418, filed Apr. 3, 2009, and PCT/US2009/0633989 filed Nov. 11, 2009, are each incorporated herein by reference in their entirety.

FIELD

The present disclosure pertains to apparatus or methods for taking blood glucose measurements, such as blood glucose meters that are at once easy to use so as to facilitate improved diabetes control in patients, and which serves more than a mere diagnostic function. In addition, the disclosure pertains to such apparatus or methods that have an improved user interface that facilitates data entry by a user, as well as programming that permits, among other things the user to override an insulin dose recommendation provided by the disclosed apparatus.

BACKGROUND

Diabetes is a chronic disease resulting from deficient insulin secretion by the endocrine pancreas. About 7% of the general population in the Western Hemisphere suffers from diabetes. Of these persons, roughly 90% suffer from Type-2 diabetes while approximately 10% suffer from Type-1. In Type-1 diabetes, patients effectively surrender their endocrine pancreas to autoimmune distraction and so become dependent on daily insulin injections to control blood-glucose-levels. In Type-2 diabetes, on the other hand, the endocrine pancreas gradually fails to satisfy increased insulin demands, thus requiring the patient to compensate with a regime of oral medications or insulin therapy. In the case of either Type-1 or Type-2 diabetes, the failure to properly control glucose levels in the patient may lead to such complications as heart attacks, strokes, blindness, renal failure, and even premature death.

Insulin therapy is the mainstay of Type-1 diabetes management and one of the most widespread treatments in Type-2 diabetes, about 27% of the sufferers of which require insulin. Insulin administration is designed to imitate physiological insulin secretion by introducing at least two classes of insulin into the patient's body: Long-acting insulin, which fulfills basal metabolic needs; and short-acting insulin (also known as fast-acting insulin), which compensates for sharp elevations in blood-glucose-levels following patient meals. Orchestrating the process of dosing these two types of insulin, in whatever form (e.g., separately or as premixed insulin) involves numerous considerations.

First, patients measure their blood-glucose-levels on average about 3 to 4 times per day. The device most commonly employed in diabetes management is the blood glucose meter. Such devices come in a variety of forms, although all are characterized by their ability to provide patients near instantaneous readings of their blood-glucose-levels. This additional information can be used to better identify dynamic trends in blood-glucose-levels. However, conventional glucose meters, in addition to other drawbacks, are designed to be diagnostic tools rather than therapeutic ones. Therefore, by themselves, even state-of-the-art glucose meters do not lead to improved glycemic control.

Many users with diabetes take one or more insulin injections daily and may use a syringe or an insulin pen to deliver the desired insulin. On average insulin-takers measure their glucose level 3 times a day using one of many commercially available glucose meters. While an insulin-taker glucose level is a diagnostic indication of glycemic control, the therapeutic action designed to achieve glycemic control is the insulin injection. Insulin-takers typically follow a dosage prescribed by a health care provider that instructs them to take a certain amount of insulin given an event (e.g., breakfast, lunch, dinner, bedtime, etc.) and potentially their present glucose level. There are several software applications that allows a physician to digitize the dosage, typically using a Personal Digital Assistant (PDA) platform, such that the user need only to point out to the current event and, if necessary, enter the current glucose level to receive an insulin dose recommendation. Such applications are generally referred to as dose-calculators. Dose-calculators exist for smartphones or iPhone.

While some insulin pump controllers connect a glucose reading with a physician programmed infusion profile yielding a suggested therapeutic action, glucose meters are diagnostic devices. People that use manual syringe injections to administer insulin rely on glucose meters to measure their current glucose level to follow a health care provider recommendation given in the form of a dosage. The task of how the information therein, i.e., a glucose level, be used is left at the hands of the users and their health care provider. Accordingly, there continues to exist the need for apparatus and/or methods that are at once easy to use so as to facilitate improved diabetes control in patients, and which serves more than a mere diagnostic function. Such apparatus will provide users with an actionable item to follow. Furthermore, the instruction can be adjusted to fit unique individualized needs of the users as reflected by historic glucose levels. The present disclosure addresses these problems and other problems that will become apparent from the discussion herein.

SUMMARY

Certain embodiments are directed to apparatus and/or methods that allow the user to proceed automatically from the determined glucose level to the event menu. Such action prompts the user attention to the fact that the apparatus at hand is more than a regular glucose meter. This simplifies the learning process of how a new apparatus should be used.

Certain embodiments describe apparatus and/or methods that connect a glucose meter and dose-calculator. These disclosed embodiments translate a drop of blood to an actionable item that is: a) whether or not insulin should be taken; and b) a recommended amount of insulin a user should take in case insulin is required.

Certain embodiments are directed to apparatus and/or methods that with a single button press the user gets a personalized insulin recommendation.

In certain embodiments, the present disclosure comprehends an apparatus for taking blood glucose measurements and recommending insulin doses, comprising:

a body for housing:
(a) a test strip port for receiving a test strip;
(b) at least a first computer-readable memory;
(c) a processor operatively connected to the at least first computer-readable memory;
(d) a display screen operatively connected to the processor so as to
successively display information displays corresponding to at least the following:
(i) a patient's current blood glucose level measurement as determined from a sample of the patient's blood provided on a test strip;
(ii) an event associated with the said current blood glucose level measurement; and
(iii) a recommended insulin dose; and
the display screen further operative to continuously display indicia corresponding to each of the said successive information displays;
(e) a plurality of user-actuated buttons operatively connected to the processor and positioned adjacent the display screen, the plurality of buttons including a first button operative to enable a user to selectively cycle through the successive information displays on the display screen, and second and third buttons operative to enable a user to selectively alter the information displayed in one or more of the successive information displays on the display screen; and
wherein the continuously displayed indicia corresponding to each of the successive information displays are positioned on the display screen in longitudinal alignment with the position of the first button, and the successively displayed information is positioned on the display screen in alignment with the second and third buttons.

In certain embodiments, the displayed indicia corresponding to each of the successive information displays may be continuous. The continuously displayed indicia corresponding to each of the successive information displays may be positioned on the display screen in longitudinal alignment with the position of the first button, while the successively displayed information may be positioned on the display screen in alignment with the second and third buttons. Other configurations are also contemplated. For example, buttons may be positioned below or above the display in such a form that does not visually align with the information on the screen in which cases buttons may include labels to identify their purpose.

In certain embodiments, the successive display on the display screen of the information display corresponding to an event associated with the said current blood glucose level measurement automatically, or substantially automatically, succeeds the display of the information display corresponding to a patient's current blood glucose level measurement if the first button is not user-actuated within a predetermined period of time.

In certain embodiments, the apparatus may be programmed to enable a user to selectively override the recommended insulin dose displayed on the display screen using one or more of the plurality of buttons.

In certain embodiments, the apparatus may comprise a labeling area on which a user may provide personalized identifying indicia.

Certain embodiments disclose an apparatus comprising: (a) a test strip port for receiving a test strip; (b) at least a first a computer-readable memory; (c) a processor operatively connected to the at least first computer-readable memory; (d) a display screen operatively connected to the processor so as to successively display information displays corresponding to at least the following: (i) a patient's current blood glucose level measurement as determined from a sample of the patient's blood provided on a test strip; (ii) an event associated with the said current blood glucose level measurement; and (iii) a recommended insulin dose; and the display screen further operative to continuously display indicia corresponding to each of the said successive information displays; (e) a plurality of buttons that may be user-activated operatively connected to the processor, the plurality of buttons including a first button operative to enable a user to selectively cycle through the successive information displays on the display screen, and second and third buttons operative to enable a user to selectively alter the information displayed in one or more of the successive information displays on the display screen; and wherein the continuously displayed indicia corresponding to each of the successive information displays are positioned on the display screen in an alignment with the position of the first button, and the successively displayed information is positioned on the display screen in an alignment with the second and third buttons.

Certain embodiments disclose an apparatus comprising: (a) a test strip port for receiving a test strip; (b) at least a first a computer-readable memory; (c) a processor operatively connected to the at least first computer-readable memory; (d) a display screen operatively connected to the processor so as to successively display information displays corresponding to at least the following: (i) a patient's current blood glucose level measurement as determined from a sample of the patient's blood provided on a test strip; (ii) an event associated with the said current blood glucose level measurement; and (iii) a recommended insulin dose; and the display screen further operative to continuously display indicia corresponding to each of the said successive information displays; (e) at least one button that may be user-actuated operatively connected to the processor, the at least one button operative to enable a user to selectively cycle through the successive information displays on the display screen.

Certain embodiments are to a method for taking blood glucose measurements and recommending insulin doses, comprising: using an apparatus comprising: (a) a test strip port for receiving a test strip; (b) at least a first a computer-readable memory; (c) a processor operatively connected to the at least first computer-readable memory; (d) a display screen operatively connected to the processor so as to successively display information displays; (e) at least one button that may be user-actuated operatively connected to the processor, the at least one button operative to enable a user to selectively cycle through the successive information displays on the display screen; obtaining a current blood glucose measurement from a blood sample and displaying that information on the display screen; displaying an event associated with the current blood glucose level measurement; optionally confirming the accuracy of the event by actuating the at least one button; and generating a dose recommendation if required.

Certain embodiments are to a method for taking blood glucose measurements and recommending insulin doses, comprising: using an apparatus comprising: (a) a test strip port for receiving a test strip; (b) at least a first a computer-readable memory; (c) a processor operatively connected to the at least first computer-readable memory; (d) a display screen operatively connected to the processor so as to successively display information displays corresponding to at least the following: (i) a patient's current blood glucose level measurement as determined from a sample of the patient's blood provided on a test strip; (ii) an event associated with the said current blood glucose level measurement; and (iii) a recommended insulin dose; and the display screen further operative to continuously display indicia corresponding to each of the said successive information displays; (e) a plurality of buttons that may be user-actuated operatively connected to the processor, the plurality of buttons including a first button operative to enable a user to selectively cycle through the successive information displays on the display screen, and second and third buttons operative to enable a user to selectively alter the information displayed in one or more of the successive information displays on the display screen; and wherein the continuously displayed indicia corresponding to each of the successive information displays are positioned on the display screen in an alignment with the position of the first button, and the successively displayed information is positioned on the display screen in an alignment with the second and third buttons; obtaining a blood glucose measurement from a blood sample and automatically displaying that information on the display screen; obtaining a recommendation on whether or not insulin should be taken and automatically displaying that information on the display screen; and if insulin should be taken displaying a recommended amount of insulin.

Certain embodiments of the present disclosure provide apparatus and/or methods that provide an intuitive and simple user interface with conspicuous features. This allows the user to rapidly familiarize themselves with the operation procedures of the device. In contrast many medical devices, such as glucose meters, include a variety of hidden features that are difficult to access, for example programmable alarms. Such design often causes frustration in the hands of end user.

Certain embodiments of the present disclosure are designed and/or configured to allow at least 70%, 80%, 85%, 90%, or 95% of intended users to become proficient in the primary operation of the apparatus after just one, two or three, test uses.

Certain embodiments are to an apparatus that provides a user interface that enables at least 85% of intended users to become proficient in the primary operation of the apparatus after two test uses.

Certain embodiments are to an apparatus that provides an intuitive and simple user interface with conspicuous features that enables at least 85% of intended users to become proficient in the primary operation of the apparatus after two test uses.

Certain embodiments are to a method that uses a user interface that enables at least 85% of intended users to become proficient in the primary operation of the apparatus after two test uses.

Certain embodiments are to a method that uses an intuitive and simple user interface with conspicuous features that enables at least 85% of intended users to become proficient in the primary operation of the apparatus after two test uses.

Preferably these test uses are conducted under the supervision of a train health care provider; however, they need not be so conducted. In its main functionality the display flow from glucose level to the event menu in a substantial automatic fashion where if the default selected event is the correct event then by pressing button 13 (see Figures) once the user receives an insulin recommendation. This design allows a substantial percentage of users from various age groups to successfully operate the apparatus within just one, two or three examples of use.

For example, when an exemplary disclosed apparatus is turned on using the on/off button 13 the display shows the present insulin therapy information. With the press of button 13 the display advances to the history screen where using buttons 14 and 15 the user can view historic glucose/insulin events. By pressing button 13 again the display advances to the change setting Y/N screen that allows the user to enter the setting menu and adjust the time and/or date. By removing any redundant functionality, e.g. alarms or display options, it is easy for the user to learn the full functionality of the device within a small number of test uses. This can be verified in a human factors analysis study where the average number of 'runs' it takes a user until he is fully fluent in the device functionality is measured. Other exemplary one button apparatus are disclosed herein as well as method of using one button apparatus and apparatus with a plurality of buttons.

Creating an easy and intuitive to use apparatus significantly reduces adoption barriers and costs of implementing a wide scale deployment effort for certain of the disclosed embodiments.

BRIEF DESCRIPTION OF THE DRAWINGS

For a better understanding of the disclosure, and to show more clearly how it may be carried into effect according to one or more embodiments thereof, reference will now be made, by way of example, to the accompanying drawings, showing exemplary embodiments of the present disclosure and in which:

FIG. 12 is an information display corresponding to a pre-mixed insulin dosage, in accordance with certain embodiments;

FIG. 13 is an information display corresponding to a dose recommendation, in accordance with certain embodiments;

FIG. 14 is an information display corresponding to a dose recommendation, in accordance with certain embodiments;

FIG. 15 is an information display corresponding to a dose recommendation, in accordance with certain embodiments;

FIG. 16 is an information display corresponding to a dosage screen for users, in accordance with certain embodiments;

FIG. 17 is an information display corresponding to a screen where user may enter the quantity of carbs, in accordance with certain embodiments;

FIG. 18 is an information display corresponding to a dose recommendation, in accordance with certain embodiments;

FIG. 22 is an information display, in accordance with certain embodiments; and

FIG. 23 is an information display, in accordance with certain embodiments.

DETAIL DESCRIPTION

The following description is provided in relation to several embodiments which may share common characteristics and features. It is to be understood that one or more features of one embodiment may be combinable with one or more features of the other embodiments. In addition, any single feature or combination of features in any of the embodiments may constitute additional embodiments. Specific structural and functional details disclosed herein are not to be interpreted as limiting, but merely as a representative basis for teaching one skilled in the art to variously employ the disclosed embodiments and variations of those embodiments.

The accompanying drawings are not necessarily to scale, and some features may be exaggerated or minimized to show details of particular components.

Figure 1:
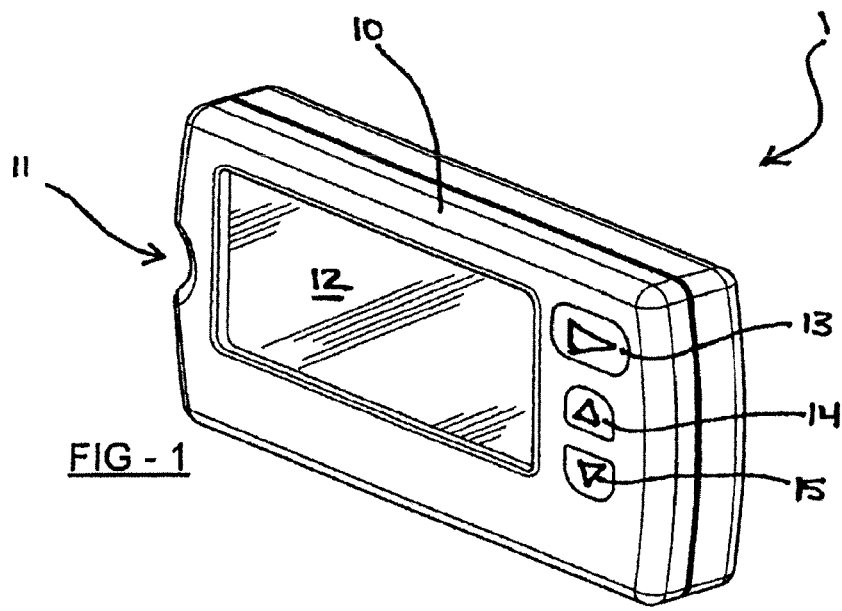
FIG. 1 is a frontal perspective view of an exemplary embodiment of the apparatus.
Figure 2:
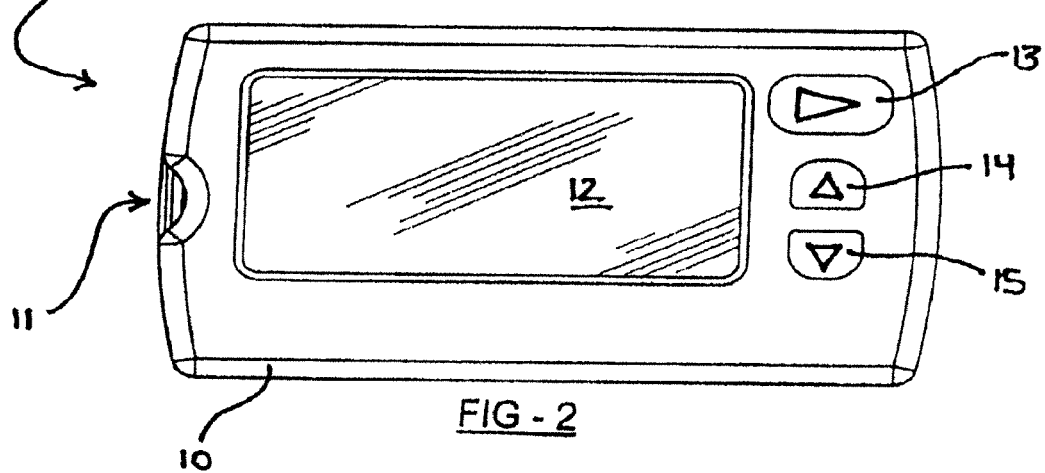
FIG. 2 is a front elevation view of the apparatus of FIG. 1.
Figure 3:
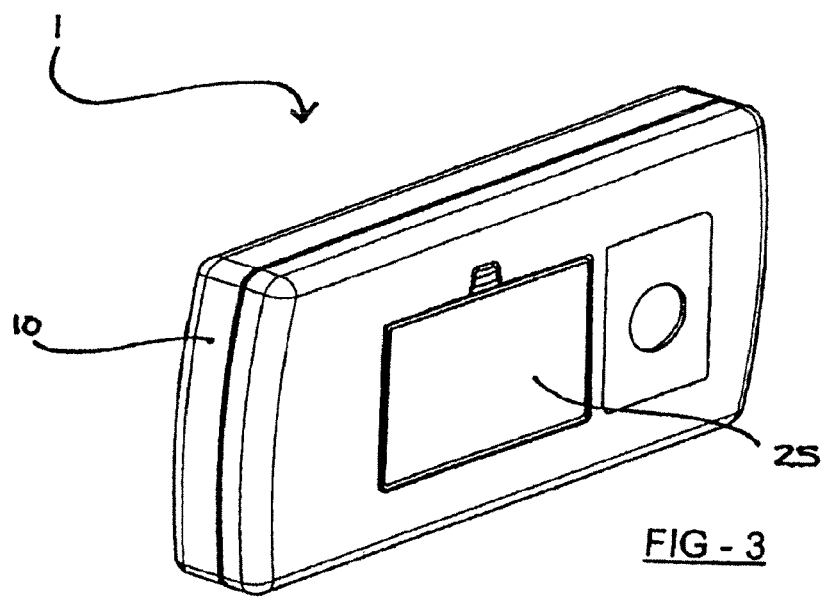
FIG. 3 is a rear perspective view of the apparatus of FIG. 1.

Referring now to the drawings, wherein like numerals refer to like or corresponding parts throughout the several views, certain embodiments of the present disclosure are directed to an apparatus 1 for taking blood glucose measurements and recommending insulin doses, the apparatus comprising a body 10 housing the following components: A test strip port 11 for receiving a test strip (not shown); at least a first computer-readable memory (not visible); a processor (not visible) operatively connected to the at least first computer-readable memory; a display screen 12 operatively connected to the processor, and a plurality of user-actuated buttons operatively connected to the processor and positioned adjacent the display screen 12, the buttons including a first button 13, and second button 14 and third button 15. In other configuration the button may be located in other arrangements and/or not be a separate physical button but could be a software programmable button located on touch screen 12. (FIGS. 1-3.) Power to the apparatus may be provided via a battery or batteries which may, for instance, be replaceable (to which end the body includes a removable cover 25 for accessing an internally disposed battery compartment). In addition to such other functions as described herein, at least one of the first 13, second 14 or third 15 buttons is operative to power the apparatus on and off (although it is also contemplated that a separate such power button or switch may be provided). In addition, or alternatively, the apparatus may be programmed to turn on automatically upon insertion of a test strip in the test strip port 11. Other power sources are also contemplated.

Display screen 12 may, by way of non-limiting example, comprise an LCD screen, the apparatus being programmed, according to convention, to display thereon such information displays as herein described.

Figure 3A:
FIG. 3*a* shows an exemplary labeling area that may be provided on the apparatus, and on which labeling area a user may provide personalized identifying indicia.
Figure 21:
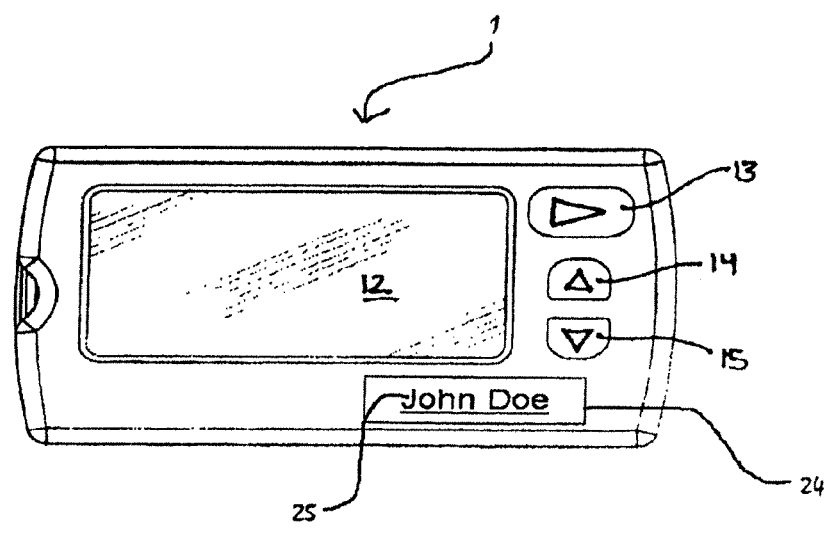
FIG. 21 shows an exemplary labeling area that may be provided on the apparatus, and on which personalized identifying indicia may be provided.

Optionally, the apparatus may be provided with a labeling area on which a user or other party may provide personalized identifying indicia. In the embodiment as shown in FIG. 3a, the labeling area may comprise an adhesive label applied to the body 10 (such as, for instance, on the back surface thereof), the label including an area for a user to write his or her name, for instance. The labeling area may take other forms than as exemplified in FIG. 3a, and may further provide for a user to include personalized identifying indicia other than, or in addition to, his or her name. See for example, FIG. 21.

Figure 6:
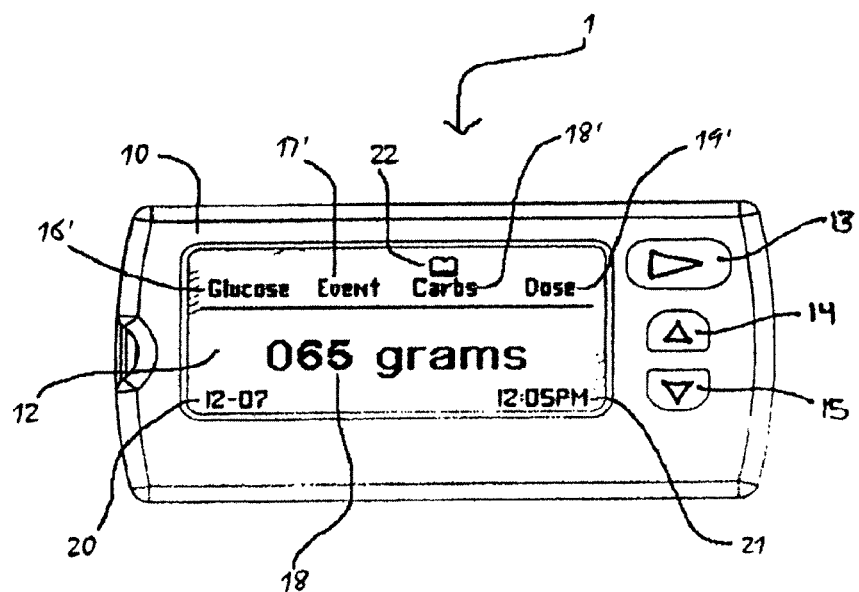
FIG. 6 depicts a third information display corresponding to a measurement for the number of carbohydrates associated with the said event, in accordance with certain embodiments.
Figure 7:
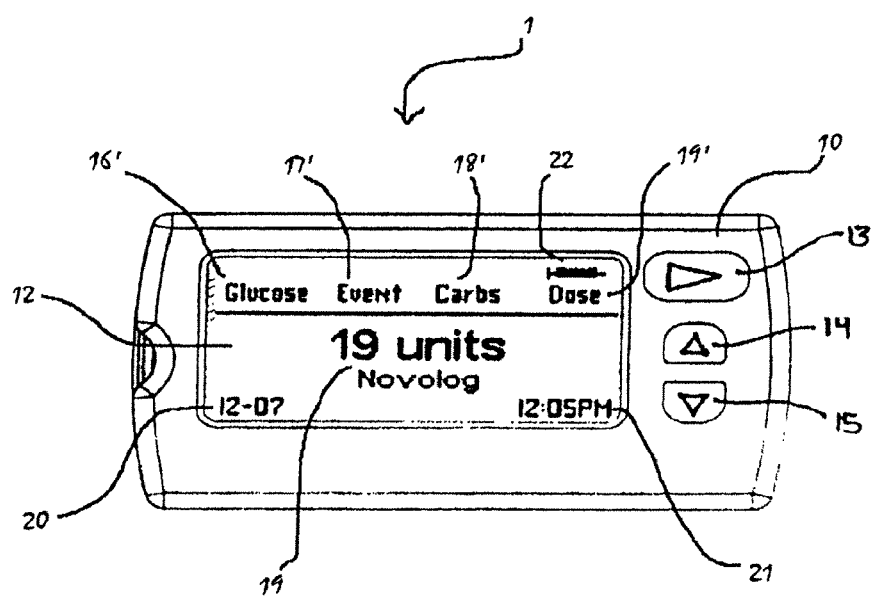
FIG. 7 depicts a fourth information display corresponding to a recommended insulin dose, in accordance with certain embodiments.

In the manner herein described, the display screen 12 is operative so as to successively display information displays corresponding to at least the following:
- a patient's current blood glucose level measurement 16 (FIG. 4);
- an event 17 associated with the said current blood glucose level measurement (FIG. 5);
- a measurement 18 for the number of carbohydrates associated with the said event (FIG. 6), if required; and
- a recommended insulin dose 19 along with a drug identifier (e.g. Novolog) (FIG. 7).

Figure 8:
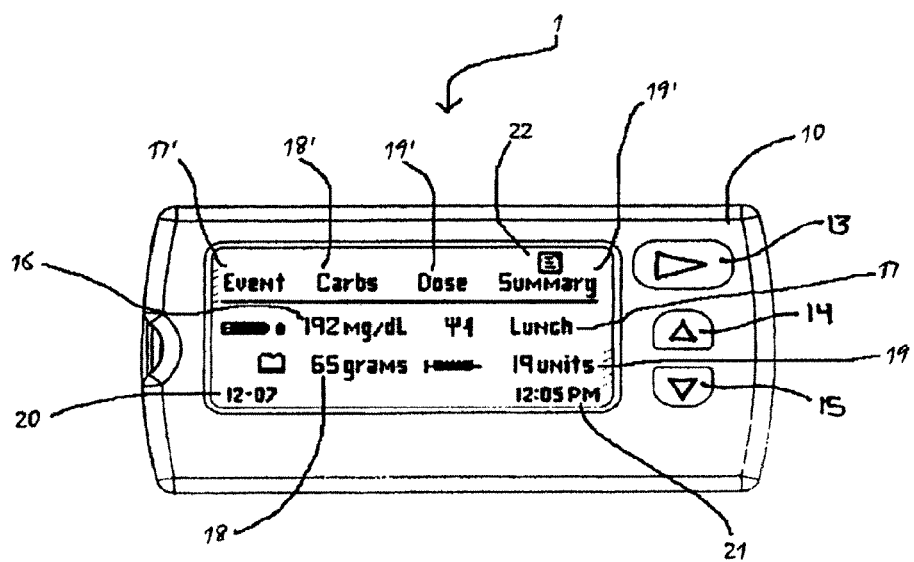
FIG. 8 depicts an optional further information display corresponding to a summary screen, in accordance with certain embodiments.

Optionally, the display screen 12 may further be operative to successively display a summary screen (FIG. 8) displaying simultaneously information corresponding to that provided on each of two or more of the foregoing information displays, including: a patient's current blood glucose level measurement, an event associated with the said current blood glucose level measurement, a measurement for the number of carbohydrates associated with the said event, and a recommended insulin dose. As shown in FIG. 8, the optional summary screen simultaneously displays information corresponding to each of a patient's current blood glucose level measurement 16, an event 17 associated with the said current blood glucose level measurement, a measurement 18 for the number of carbohydrates associated with the said event, and a recommended insulin dose 19.

As also depicted, the display screen may, optionally; continuously display in each of the information displays each of the current date 20 and time 21.

Furthermore, the display screen 12 is operative to continuously (provided the apparatus is turned on) display indicia corresponding to each of the said successive information displays; namely, indicia 16' corresponding to the information display for the patient's current blood glucose level measurement 16, indicia 17' corresponding to the information display for the event 17 associated with the said current blood glucose level measurement, indicia 18' corresponding to the information display for the measurement 18 for the number of carbohydrates associated with the said event, and indicia 19' corresponding to the information display for the recommended insulin dose 19. See FIGS. 4 through 8.

Also in the manner hereafter described, the first button 13 is operative to enable a user to selectively cycle through the successive information displays on the display screen 12, while the second 14 and third 15 buttons are operative to enable a user to selectively alter the information displayed in one or more of the successive information displays on the display screen 12.

To facilitate the successive display of the various information displays as herein described, the continuously displayed indicia 16', 17', 18' and 19' are, as shown in each of FIGS. 4 through 7, positioned on the display screen 12 in longitudinal alignment with the position of the first button 13, while the successively displayed information 16, 17, 18 and 19 is positioned on the display screen 12 in alignment with the second 14 and third 15 buttons. Such visual alignment between displayed content and button locations significantly improves usability of the apparatus. Other arrangements may also be used.

With continuing reference to FIGS. 4 through 8, the manner of operation of certain embodiments will be better understood.

Figure 4:
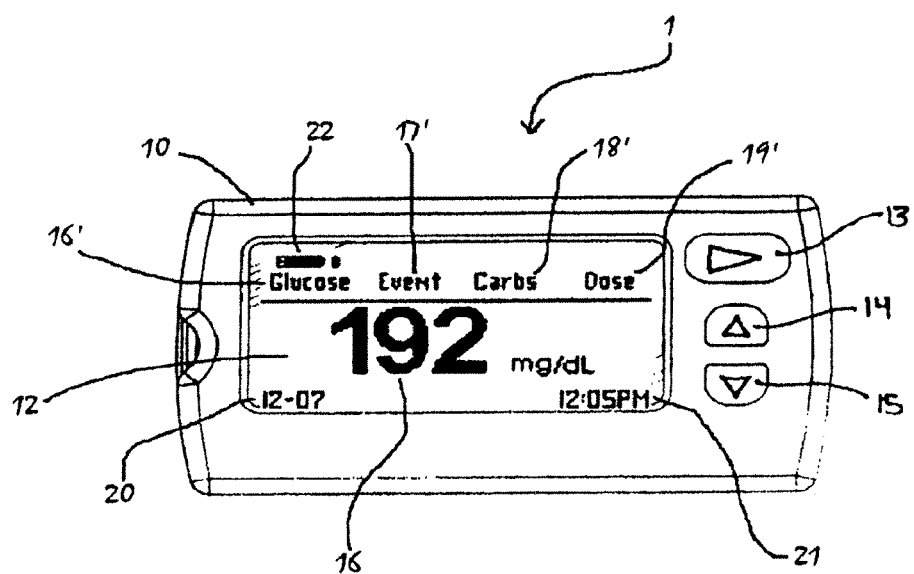
FIG. 4 depicts a first information display corresponding to a patient's current blood glucose level measurement as determined from a sample of the patient's blood provided on the test strip, in accordance with certain embodiments.

In known fashion, a user obtains a drop of his or her blood on a disposable test strip via operation of, for example, a lancet device. The test strip is inserted into the test strip port 11 and, upon determination thereafter of the blood glucose measurement from the blood sample, the information display displaying the determined blood glucose measurement 16 is automatically first displayed on display screen 12 (FIG. 4).

Figure 5:
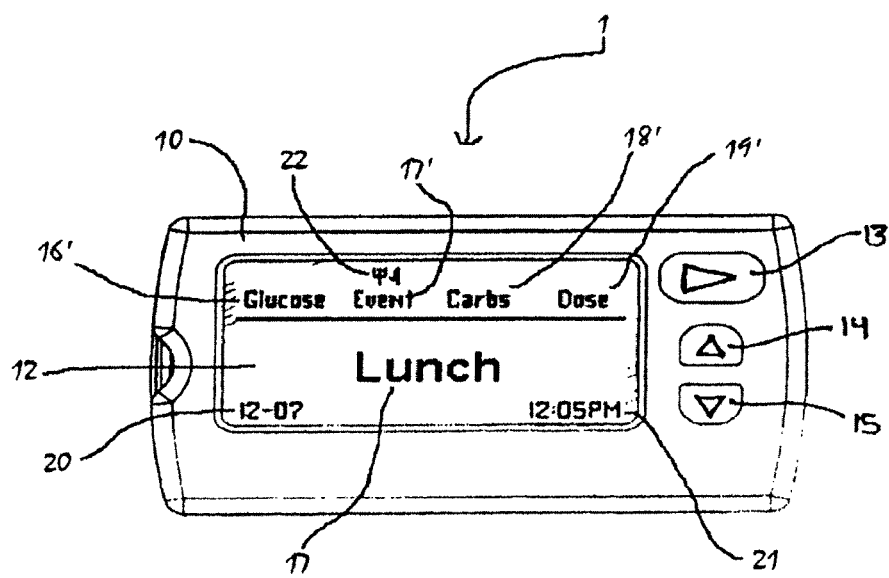
FIG. 5 depicts a second information display corresponding to an event associated with the said current blood glucose level measurement, in accordance with certain embodiments.

By actuating the first button 13, the user can transition from the information display displaying the determined blood glucose measurement 16 to the successive information display displaying the event 17 associated with the current blood glucose level measurement (FIG. 5).

Optionally, the successive display on the display screen 12 of the information display displaying information corresponding to the event 17 associated with the current blood glucose level measurement 16 automatically succeeds the display on the display screen 12 of the patient's current blood glucose level measurement 16 if the first button 13 is not user-actuated within a predetermined period of time (e.g., 3 seconds). In this fashion, the user may be automatically prompted to input data (i.e., the event information) into the apparatus so that these data are not omitted.

Upon reaching, by either of the foregoing routes, the information display displaying information corresponding to the event 17 associated with the current blood glucose level measurement (FIG. 5), the user is able to select an appropriate event (e.g., breakfast, lunch, dinner) associated with the previously displayed blood glucose measurement 16 by scrolling, using the second and third buttons, up and down, respectively, through a preprogrammed list of events (e.g., lunch, as shown in FIG. 5) successively displayed on the display screen 12 with each successive actuation of one of the second 14 and third 15 buttons.

Subsequent to selection of an event associated with the current blood glucose level measurement, the user can, by actuating the first button 13, transition from the information display displaying the event 17 associated with the blood glucose measurement to the successive information display displaying information corresponding to a measurement 18 for the number of carbohydrates associated with the event 17 (FIG. 6). It is contemplated that, in certain embodiments upon each actuation of the first button 13 to transition from one information display to the next, the apparatus may be programmed to automatically store in memory user-defined data as selected, for example, in the immediately preceding information display (such as, for instance, the user-elected event in the information display of FIG. 5). Upon reaching this next information display, the user is presented with the value '000' 18 in FIG. 6 corresponding to the previously selected event (e.g., lunch). The user is further able to modify the 000 measurement 18 by scrolling up and down using the second 14 and third 15 buttons effecting, respectively, an incremental (e.g., by a single integer) increase or decrease in the predefined measurement 18.

Subsequent to having reviewed and, optionally, modified measurement 18 displayed on the information display displaying information corresponding to the measurement 18 for the number of carbohydrates associated with the event 17, the user can, by actuating the first button 13, transition from that information display to the successive display on the display screen 12 of the information display displaying information corresponding to the recommended insulin dose 19 (FIG. 7). Upon reaching this next information display, the user is presented with information corresponding to a recommended insulin dose 19 (e.g, 19 units in FIG. 7) calculated according to the information previously input by the user, such as, for instance, according to the inventions as described in US Published Applications 20090253970 and 20090253973, the disclosures of which published patent applications are incorporated herein by reference in their entireties (and according to which inventions the present inventions may in other respects not expressly disclosed herein operate like). The user may then, at his or her discretion, administer the recommended insulin dose 19.

Optionally, the apparatus 1 is programmed to enable a user to selectively override the recommended insulin dose 19 information displayed on the display screen 12 using one or more of the plurality of buttons 13, 14 and 15 and, according to the illustrated embodiment more particularly, using the second 14 and third 15 buttons. More specifically, the user is further able to modify the recommended insulin dose 19 by scrolling up and down using the second 14 and third 15 buttons, with each successive actuation of one of the second 14 and third 15 buttons effecting, respectively, an incremental (e.g., by a single integer) increase or decrease in the recommended insulin dose 19.

Subsequent to having reviewed and, optionally, modified the information corresponding to a recommended insulin dose 19 displayed on the information display, the user can, by actuating the first button 13, transition from that information display to the successive, optionally provided a summary screen (FIG. 8).

It is contemplated that in certain embodiments when the apparatus 1 is turned on, the default information display displayed on the display screen 12 will be one of the summary screen (FIG. 8) or the information display displaying information corresponding to the determined blood glucose measurement 16 (FIG. 4). Where the default information display is the summary screen (FIG. 8), it is further contemplated that display of the information display displaying information corresponding to the determined blood glucose measurement 16 (FIG. 4) will occur automatically upon a new determination of a patient's blood glucose measurement triggered by an insertion of a test strip.

As is shown in each of FIGS. 4 through 7, the continuously displayed indicia 16', 17', 18' and 19' are positioned on the display screen 12 in each of the on screen displays of FIGS. 4 through 7 and, moreover, that indicia 22 (which may be the same or, as depicted, different indicia) are provided proximate one of the continuously displayed indicia 16', 17', 18' and 19' corresponding to the information display presently being displayed on the display screen 12. In this manner, clear indication is given to the user as to which information display is currently provided on display screen 12 and, since the continuously displayed indicia 16', 17', 18' and 19' are arranged longitudinally according to their successive order of appearance upon actuation of first button 13, which information display will be displayed next upon user actuation of the first button 13. Furthermore, it will be appreciated from the disclosure herein that by displaying the continuously displayed indicia 16', 17', 18' and 19' in longitudinal alignment with the position of the first button 13 on the body 10, it will be intuitive to a user that actuation of the first button 13 will effect linear cycling of the information displays according to the linear presentation of the continuously displayed indicia 16', 17', 18' and 19'.

Similarly, it will be appreciated from the disclosure herein that by displaying the particular information of each of the successive information display 16, 17, 18 and 19 in alignment with the position of the second 14 and third 15 buttons on the body 10, it will be intuitive to a user that actuation of these buttons will effect modification in the respective information displayed in these information displays.

The following examples, further illustrate certain embodiments of the devices and/or methods disclosed herein. These examples illustrate how the device and/or method may be used to support four types of insulin regimens: Basal only, pre-mixed insulin, Basal-Bolus using a sliding scale, and Basal-Bolus using carbohydrate counting and/or a sliding scale.

Basal insulin therapy typically includes a daily dosage of one type of insulin that can be administered by a single injection. For example, a prescription (dosage) may require a patient to administer 28 units of Lantus® once a day. Patients following this regimen are typically recommended to measure their fasting glucose level each morning and to administer 28 units once a day regardless of the glucose readings. Glucose readings can be used by a healthcare provider to adjust the dosage (in this case the number 28) during the next clinic visit.

Figure 9:
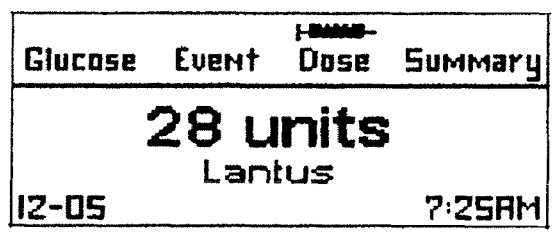
FIG. 9 is an information display corresponding to a recommended insulin dose, in accordance with certain embodiments.

The device is typically initially programmed or set up by the health care provider. In this example the devise is programmed with the drug information Lantus® and the daily dosage 28 units. The device recommends that this daily injection be administered in the morning soon after the user measures fasting glucose level. The user will see, for example, the screen depicted in FIG. 9 after a morning glucose measurement. The recommendation in this example is to take 28 units of Lantus® (as the current dosage prescribes) regardless of the latest blood glucose level.

Figure 10:
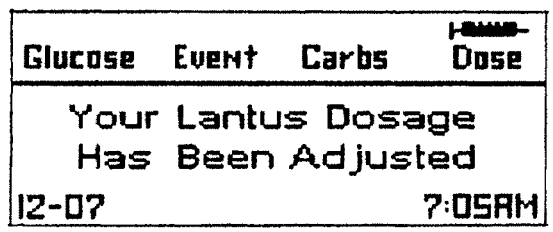
FIG. 10 is an information display corresponding to a dosage adjustment message, in accordance with certain embodiments.
Figure 11:
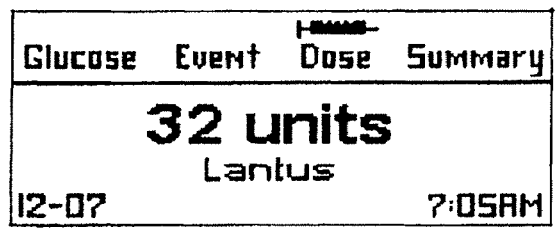
FIG. 11 is an information display corresponding to a new dose recommendation, in accordance with certain embodiments.

Periodically, for example, on a weekly basis, the device evaluates the glucose readings in memory and may adjust if desired the current dosage. For example, if glucose readings in the relevant period are above target, the device may use the Frequently-Adjusted-Insulin-Therapy-Heuristics (FAITH™) software or other appropriate software might increase the daily dosage from 28 to 32 units of Lantus®. If so, the user will see an indication that the Lantus dosage has been adjusted as seen in FIG. 10. This may be followed by the dose screen shown in FIG. 11 with the new dose recommendation of 32 units Lantus.

Pre-mixed insulin therapy is typically given with two daily injections of a single drug such as Novolog® Mix 70/30. Patients using this regimen typically are required to measure their glucose levels before every injection, i.e., twice a day. Pre-mixed insulin is a mixture of intermediate- and fast-acting insulin formulations designed to compensate for basal needs as well as for meals. For example, a prescription (dosage) can require a user to administer 72 units with breakfast and 32 units with dinner such as recommended in FIG. 12 on the device's dosage screen. In this illustrated example a measurement tagged as Breakfast by the device (with possible manual tagging by the user) will result in a recommendation to administer a dose of 72 units of Novolog Mix 70/30 as seen, for example, in FIG. 13, regardless of the blood glucose level. As with Basal insulin therapy, the blood glucose levels stored in memory may be used by a healthcare provider to adjust the aforementioned dosage during clinic visits.

The FAITH™ software or other appropriate software may periodically assess the efficacy of the prescribed medication dosage and may decide to adjust it from time to time. For example, if blood glucose levels at breakfast are below target, FAITH™ or some other appropriate software may decrease dinner dosage from 32 units to 30 units. In such a case the user is advised that a change has been made to the dosage and the next measurement tagged as Dinner will result in the new recommendation to administer 30 units of Novolog® Mix 70/30.

Basal-Bolus insulin therapy is designed to typically mimic the natural behavior of the pancreas. Patients adhering to this regimen may be required to measure their blood glucose level before every meal and at bedtime, and to administer a dose of fast-acting insulin based on their pre-meal measurements. In addition, they may be required to administer a fixed dose of long-acting insulin once a day, typically at bedtime. A dosage example may include taking 36 units of Lantus® (long-acting insulin) at bedtime and the sliding scale given in Table 1 with meals. Table 1 below shows Bolus insulin dosage examples using a sliding scale. Doses are in insulin units [IU]. This sliding scale can be summarized as 12, 13, and 12 units of fast-acting insulin for normal blood glucose measurements (between 80-120 mg/dl) with breakfast, lunch, and dinner, respectively plus (minus) one unit of fast-acting insulin for every 20 mg/dl of blood glucose level above 120 mg/dl.

TABLE 1

| Glucose level (mg/dl) | | Breakfast | Lunch | Dinner |
| --- | --- | --- | --- | --- |
| Low | High | [IU] | [IU] | [IU] |
| 60 | 80 | 11 | 12 | 11 |
| 81 | 120 | 12 | 13 | 12 |
| 121 | 140 | 13 | 14 | 13 |
| 141 | 160 | 14 | 15 | 14 |
| 161 | 180 | 15 | 16 | 15 |
| 181 | 200 | 16 | 17 | 16 |
| 201 | 220 | 17 | 18 | 17 |
| 221 | 240 | 18 | 19 | 18 |
| 241 | 260 | 19 | 20 | 19 |
| 261 | 280 | 20 | 21 | 20 |
| 281 | 300 | 21 | 22 | 21 |
| 301 | | 22 | 23 | 22 |

For such cases, the device will calculate the required bolus dose based on a pre-meal blood glucose measurement, the meal to which it is tagged, and the current dosage (Table 1) stored in memory. If a user is about to have breakfast and the pre-meal glucose reading is 209 mg/dl the device will generate the recommendation shown in FIG. 14. That recommendation is to take a dose of 17 units of fast-acting insulin (Novolog®) based on the dosage in Table 1 and a pre-breakfast glucose reading between 201 and 220 mg/dl. The user does not have to carry the table (dosage) on a separate sheet as it is stored on the device memory. The user does not have to count the carbohydrate content of each meal or to be asked for such information by the device. When a measurement is tagged as Bedtime, the device will recommend taking 36 units of long-acting insulin based upon the current dosage and depicted, for example, in FIG. 15.

Periodically the FAITH™ software or other appropriate software embedded in the device may evaluate the efficacy of the prescribed dosage using the recent blood glucose levels stored in the device memory. Such evaluation may result in an adjustment to one or more components of the current dosage. An adjustment may be to increase dosage of long-acting insulin to 40 units at bedtime or to increase/decrease the entries in Table 1. For example, an updated 'breakfast' dosage may be 11 units of fast-acting insulin for normal blood glucose levels plus (minus) one unit of fast-acting insulin for every 30 mg/dl above 120 mg/dl. This modified sliding scale or updated dosage is given in Table 2 and will result in a recommendation to administer 14 units of Novolog® for a pre-breakfast measurement of 209 mg/dl (compared to 17 units with the previous dosage). In this particular example, the modified table is not available for the user on screen. Instead, it is available by accessing the dosage screen seen, for example, in FIG. 16 which shows the dosage screen for users following Basal-Bolus therapy using a sliding scale.

TABLE 2

| Glucose level (mg/dl) | | Breakfast | Lunch | Dinner |
| --- | --- | --- | --- | --- |
| Low | High | [IU] | [IU] | [IU] |
| 60 | 80 | 10 | 12 | 11 |
| 81 | 120 | 11 | 13 | 12 |
| 121 | 150 | 12 | 14 | 13 |
| 151 | 180 | 13 | 15 | 14 |
| 181 | 210 | 14 | 16 | 15 |
| 211 | 240 | 15 | 17 | 16 |
| 241 | 270 | 16 | 18 | 17 |
| 271 | 300 | 17 | 19 | 18 |
| 301 | | 18 | 20 | 19 |

It would be appreciated that for a user of an apparatus programmed with one or more of the aforementioned three insulin regimens would skip the process illustrated in FIG. 6. For users who follow these regimens the natural sequence is from the event menu depict in FIG. 5 to an insulin recommendation, if required, depict in FIG. 7.

It would further be appreciated that default event selection can be associated with the apparatus internal clock as suggested by Table 5. In such cases, since the apparatus may proceed to the event menu in a substantially automatic manner and when the default event displayed on the screen is the correct event then by a single press of Button 13 displayed in FIG. 5 the apparatus proceed to provide the user with the actionable item displayed in FIG. 7, i.e. a recommendation to take 19 units of Novolog®. Accordingly, such apparatus is user-friendly, easy and intuitive to use, and provides a person following insulin therapy with the most pertinent information: how many units of insulin they need to administer.

In comparisons to the previous regimen where a patient's meal content is assumed to be relatively stable depending only on which meal, this regimen prescribes patient insulin in a proportional manner to the content of each meal. Patients on this regimen (i.e. Basal-Bolus Insulin Therapy using Carbohydrate Counting and a sliding scale) are typically prescribed with a fixed dosage of long-acting insulin taken daily plus a ratio of insulin units to carbohydrates (carbs) for each meal and a correction factor to compensate for elevated pre-meal blood glucose levels. Such prescription may be 55 units of long-acting insulin at bedtime and a fast-acting insulin to carb ratio of 1:8, 1:5, and 1:15 for breakfast, lunch, and dinner, respectively along with one additional unit of fast-acting insulin for every 30 mg/dl of blood glucose level above 120 mg/dl. Patients following this regimen are typically required to count carbs of each meal in addition to measuring their blood glucose level before a meal (and at bedtime) to figure out how many units of fast-acting insulin to administer. For example, if a patient is about to consume 65 grams of carbohydrate for lunch and the pre-lunch glucose level is 294 mg/dl the patient has to administer 19 units of fast-acting insulin: 13 units are to compensate for a planned meal containing 65 grams of carbs (at a ratio of 1:5) plus 6 units to compensate for the pre-lunch elevated glucose level of 292 (since 292-120=174 and the dosage requires 1 unit for every 30 mg/dl above 120). The device will prompt users following this regimen to enter the quantity (in grams) of carbs they are about to consume as seen, for example, in FIG. 17. According to the current dosage, a planned lunch of 65 grams of carbs, and a pre-lunch glucose reading of 292 mg/dl the user then receive the recommendation shown in FIG. 18. FIG. 18 recommends that a user administer 19 units of fast acting insulin per a pre-lunch glucose value of 292 mg/dl and the reported 65 grams of carbs to be consumed at lunch.

Periodically, FAITH™ software or other appropriate software may use the glucose reading in memory to adjust the current dosage. Adjustment may be made to the long-acting insulin taken at bedtime, to the correction factor, and to each ratio of insulin-to-carbs composing the current dosage. For example, if pre-diner readings are low in a given period, the current lunch insulin-to-carbs ratio may be modified from 1:5 to 1:6 resulting in less fast-acting insulin recommended for future lunch doses. Such a change will generate a recommendation administer 16 units of fast-acting insulin for a planned lunch containing 65 grams of carbs and with a pre-lunch glucose level of 292 mg/dl (the new ratio would require 10 units of insulin to compensate for lunch rather than 13 units per the previous dosage).

Certain disclosed embodiments are directed to devices and/or methods that translate a drop of blood to a personalized insulin recommendation. This may be achieved with a single button devise or a device with a plurality of buttons as disclosed herein.

Figure 19:
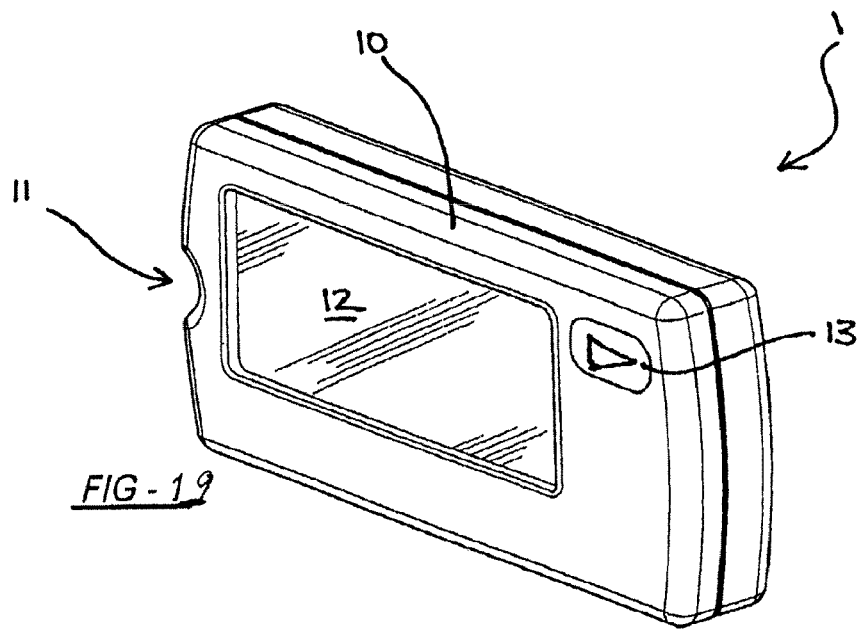
FIG. 19 is a frontal perspective view of an exemplary embodiment of the device, according to certain embodiments.
Figure 20:
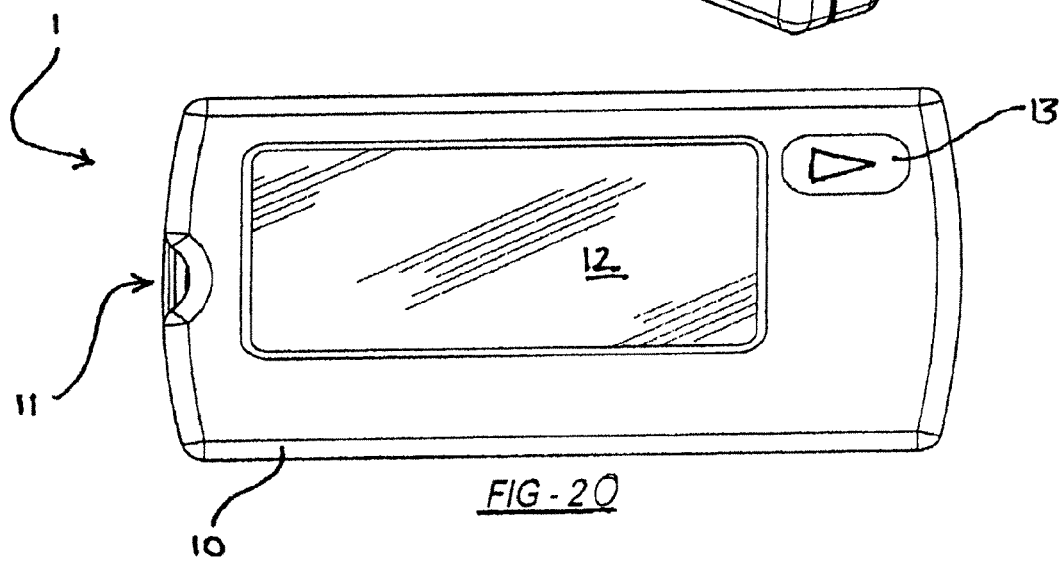
FIG. 20 is a front elevation view of the apparatus of FIG. 19.

With respect to embodiments that can achieve the desired results with only one button, FIGS. 19 and 20, illustrate a version of a device that functions with only one button. Other configurations of the device are also possible. For example, the button may not be a separate physical button but could be a software programmable button located on touch screen 12. The use of a one button device has certain advantages for the user, for example, simplicity: users may prefer less a complicated device that does not require them to enter any data. It would be appreciated that some individuals may prefer a dedicated one-task like device that can be intuitively used. These devices and/or methods use at least an insulin dosage and a blood glucose value. Certain embodiments of the one button device may support at least three insulin regimens: 1) basal only; 2) premixed; and 3)

basal-bolus that does not require carbohydrate counting. Other embodiments disclosed herein may support a number of varying regimens whether single button devices or devices with a plurality of buttons. Insulin regimen one and two may depend on an event, or at least one event, to provide the user with the appropriate insulin dose recommendation. Regimen three typically needs both event information and current blood glucose level to provide an adequate recommendation. To illustrate the application of certain embodiments, Table 3 below describes a list of events per regimen and Table 4 describes which event requires a dose recommendation per regimen. For example a 'Dinner' event requires a dose recommendation for both regimens 2 and 3 and is in this example is not applicable for regimen 1.

TABLE 3

Event by regimen

| Regimen 1 | Regimen 2 | Regimen 3 |
|---|---|---|
| Other | Other | Other |
| Nighttime | Nighttime | Nighttime |
| Bedtime | Dinner | Bedtime |
| Breakfast | Breakfast | Dinner |
|  |  | Lunch |
|  |  | Breakfast |

TABLE 4

Dose requirement per event

| Regimen | Breakfast | Lunch | Dinner | Bedtime | Nighttime | Other |
|---|---|---|---|---|---|---|
| Regimen 1 | YES | N/A | N/A | NO | NO | NO |
| Regimen 2 | YES | N/A | YES | N/A | NO | NO |
| Regimen 3 | YES | YES | YES | YES | NO | NO |

Table 5 exemplifies a mechanism to automatically, or substantially automatically, select an appropriate event for each regiment as a function of the time of day. This way the correct event can be selected without user intervention. For each regimen once the event has been selected a dose recommendation can be issued, if required.

TABLE 5

Default event selection by time of day

| | Default EVENT MENU Selection by regimen | | |
|---|---|---|---|
| Time (24 hours) | Regimen 1 | Regimen 2 | Regimen 3 |
| 05:00-9:59:59 | Breakfast | Breakfast | Breakfast |
| 10:00-10:59:59 | Other | Other | Other |
| 11:00-13:59:59 | Other | Other | Lunch |
| 14:00-16:59:59 | Other | Other | Other |
| 17:00-19:59:59 | Other | Dinner | Dinner |
| 20:00-20:59:59 | Other | Other | Other |
| 21:00-00:59:59 | Bedtime | Other | Bedtime |
| 01:00-04:59:59 | Nighttime | Nighttime | Nighttime |

The exemplified one button device has at least two modes: 'dosage' and 'testing'. As illustrated in FIGS. 19 and 20, when the device is off and button 13 is pressed the device enters 'dosage' mode where the current insulin dosage is displayed on the screen. When a test strip is being inserted at port 11 the device enters testing mode. To turn the device off, at either mode, the user presses and holds the button for a short period of time such as two seconds.

At testing mode the user is prompt to test his glucose by applying blood to the test strip. Once a glucose value is available it is displayed on the screen 12. In this example, after a short period of time such as few seconds the screen presents the automatically selected event according to Table 5. By pressing the button the user confirms the accuracy of the automatically selected event and if required a dose recommendation is generated. In this example, the recommended dose is based on the current dosage stored in memory, the confirmed event, and the current glucose level (for regimen 3 bolus dose only).

The present disclosure provides several advantages, for example, one advantage of the disclosed apparatus and/or methods is that it saves the need to carry two separate apparatus: a glucose meter and a PDA. Another advantage of the disclosed apparatus and/or methods is that it is a dedicated device and therefore much simpler to operate compared to a PDA/meter combination.

Yet another advantage of the disclosed apparatus and/or methods is that it requires a much simpler hardware and is therefore both easier and less expensive to develop and manufacture.

The disclosed apparatus and/or methods may further include safety features that prevent the user from receiving an insulin recommendation in case of a glucose level that is relatively low, for example below 65 mg/dl (yet other values such as 75, 70, 60 can be used). Such feature provides an extra safety benefit since certain embodiments of the disclosed apparatus and/or methods ties insulin recommendations with a minimal present glucose value. In this example, a health care provider may prescribe a user with the instruction to take 10 units of Humalog® with each meal provided that their pre-prandial glucose level is greater than, say, 65 mg/dl. In case that a pre-prandial glucose level is 60 mg/dl it is up to the user to remember that instruction not to take insulin. On the contrary the disclosed apparatus ties the insulin recommendation with the health care prescribed dosage to the current glucose reading. For example, if the glucose reading is 60 mg/dl the device may proceed to the screen depict in FIG. 22 rather than to FIG. 7. By doing so the apparatus alerts the user that given the current glucose level it is not safe to administer insulin. By stopping the sequence at FIG. 22 or, with the press of button 13, proceeding to FIG. 23 an insulin recommendation is no longer provided to the user.

Certain embodiments disclosed devices and/or methods wherein the visual alignment between button location and button functionality simplifies the user experience. Simplicity of use is yet another advantage of the disclosed apparatus since it simplifies the transition from known devices to new devices and/or methods that are easier to use and/or minimizes the need for user education In certain embodiments of the present disclosure the display has two distinct sections: a navigation bar and a dynamic content area. This distinction, along with the visual alignments of the button 13 to the navigation bar and buttons 14 and 15 to the dynamic content area help to create a consistent, simple, and intuitive user interface. Consider the fact that many insulin-takers are older and are frustrated by the nature of dynamic buttons, for example, as commonly used in cellular phones. Dynamic buttons change their functionality based on the button label that appears on the display adjacent to the physical button. Such dynamic user interface may confuse potential users. The disclosed apparatus has a simple and consistent design where button 13 is used to move forward along the tabs displayed on the navigation bar. And, buttons 14 and 15 are used to manipulate the information presented in the content area of the display. This design approach is different from the prior art that often used multi purpose buttons.

Certain embodiments tie glucose events to an insulin regimen. Therefore a user following a basal only regimen can tag his reading as either breakfast (fasting glucose), bedtime, nighttime, or simply other. Such tagging allows for a better interpretation of the historic data when evaluated in order to adjust insulin dosage or just to better understand the efficacy of current dosage. Current blood glucose meters in the art tag glucose measurements based on the user activity. For example, most existing glucose meters allow the user to tag glucose levels as either pre- or post-prandial. Accordingly, a user on a regimen requiring two insulin injections per day: before breakfast and before dinner will tag a glucose reading at lunch as either a pre or post meal event. Data management software packages, readily available, by most glucose meters manufacturers then allows for profiling of historic glucose reading based on their tags, e.g. display a pre-prandial profile of the last 30 days. Such profile will include pre-breakfast, pre-lunch, and pre-dinner glucose levels that were tagged by the user as pre-prandial. However, the pre-lunch reading often has little bearing on the user insulin profile and when used in conjunction with the rest of the pre-prandial readings may cause the data interpreter, either health care provider or the user, to misjudge the existing data leading to erroneous conclusions or worse erroneous dosage adjustment.

Another advantage of certain embodiments is the exclusiveness. The user is encouraged to use a single device for his/her glucose testing. Since many insulin-takers possess several glucose meters (one at home, one at the car, one at work, etc.) that they alternate between. In such cases a single device may not contain as complete historic ensemble of glucose data as may be desirable. Certain disclosed apparatus, particularly when it adjusts user insulin dosage to compensate for the individual needs, encourage the user to use it exclusively for all glucose tests. Hence, it encourages the creation of a single database containing the user's historic data.

Furthermore, since certain embodiments of the disclosed apparatus can potentially contain personally tailored medication dosage it is desirable that it is easily identifiable. Since devices made by the same manufacturer on a single product line may all look the same certain disclosed apparatus include an adhesive sticker that can be used to be placed on the front side of the device where the device owner is given a place to write his/her name. Such example is described in FIG. 21 where the sticker 24 is attached to device and a user name 25 is written on the sticker. Other means may be used with the device to provide a unique identification with its user such as a digital presentation of the user's name on the device screen.

In the following, further embodiments are explained with the help of subsequent examples.

Example 1. An apparatus comprising:
(a) a test strip port for receiving a test strip;
(b) at least a first a computer-readable memory;
(c) a processor operatively connected to the at least first computer-readable memory;
(d) a display screen operatively connected to the processor so as to successively display information displays corresponding to at least the following:
  (i) a patient's current blood glucose level measurement as determined from a sample of the patient's blood provided on a test strip;
  (ii) an event associated with the said current blood glucose level measurement; and
  (iii) a recommended insulin dose; and
  the display screen further operative to continuously display indicia corresponding to each of the said successive information displays;
(e) a plurality of buttons that may be user-activated operatively connected to the processor, the plurality of buttons including a first button operative to enable a user to selectively cycle through the successive information displays on the display screen, and second and third buttons operative to enable a user to selectively alter the information displayed in one or more of the successive information displays on the display screen; and
wherein the continuously displayed indicia corresponding to each of the successive information displays are positioned on the display screen in an alignment with the position of the first button, and the successively displayed information is positioned on the display screen in an alignment with the second and third buttons.

2. The apparatus of example 1, wherein the display screen operatively connected to the processor so as to successively display information displays corresponding to at least the following:
  (i) a patient's current blood glucose level measurement as determined from a sample of the patient's blood provided on a test strip;
  (ii) an event associated with the said current blood glucose level measurement;
  (iii) an estimate for the number of carbohydrates associated with the said event; and
  (iv) a recommended insulin dose.

3. The apparatus of examples 1 or 2, wherein the successive display on the display screen of the information display corresponding to an event associated with the said current blood glucose level measurement automatically succeeds the display of the information display corresponding to a patient's current blood glucose level measurement if the first button is not user-actuated within a predetermined period of time.

4. The apparatus of examples 3 or 4, wherein the apparatus is programmed to enable a user to selectively override the recommended insulin dose displayed on the display screen using one or more of the plurality of buttons.

5. The apparatus of examples 1-3, or 4, wherein the apparatus comprises a labeling area on which personalized identifying indicia may be provided.

6. The apparatus of examples 1-4, or 5, wherein the estimation of the number of carbohydrates associated with the said event is a measurement of the number of carbohydrates.

7. The apparatus of examples 1-5, or 6, wherein the plurality of user-actuated buttons operatively connected to the processor are positioned adjacent the display screen.

8. The apparatus of examples 1-6, or 7, wherein the continuously displayed indicia corresponding to each of the successive information displays are positioned on the display screen in said alignment that is longitudinal with the position of the first button.

9. The apparatus of examples 1-7, or 8, wherein the continuously displayed indicia corresponding to each of the successive information displays are positioned on the display screen in said alignment with the position of the first button and the successively displayed information is positioned on the display screen in a longitudinal alignment with the second and third buttons.

10. The apparatus of examples 1-8, or 9, wherein the continuously displayed indicia corresponding to each of the successive information displays are positioned on the display screen in an alignment that is longitudinal with the position of the first button. and the successively displayed information is positioned on the display screen in a longitudinal alignment with the second and third buttons.

11. The apparatus of examples 1-9, or 10, wherein the plurality of user-actuated buttons are arranged such that it is intuitive to a user that actuation of each of these buttons will effect modification in each of the associated information displays.

12a. The apparatus of examples 1-10, or 11, wherein the visual alignment between the plurality of user-actuated buttons and the associated information displays results in a user-friendly and intuitive to use apparatus.

13. The apparatus of examples 1-11, or 12, wherein the display screen is divided into two distinct sections including a navigation bar section and a dynamic content section.

14. The apparatus of examples 1-12, or 13, wherein the at least one of the user-actuated buttons is a software programmable button located on a display screen.

15. The apparatus of examples 1-13, or 14, wherein the apparatus enables at least 85% of intended users to become proficient in the primary operation of the apparatus after two test uses.

16. The apparatus of examples 1-14, or 15, wherein the apparatus is intuitive and simple to use with conspicuous features on the display screen and the apparatus enables at least 85% of intended users to become proficient in the primary operation of the apparatus after two test uses.

17. The apparatus of examples 1-13, or 14, wherein the apparatus enables at least 70%, 80%, 85%, 90%, or 95% of intended users to become proficient in the primary operation of the apparatus after one, two or three test uses.

Example 18. An apparatus comprising:
(a) a test strip port for receiving a test strip;
(b) at least a first a computer-readable memory;
(c) a processor operatively connected to the at least first computer-readable memory;
(d) a display screen operatively connected to the processor so as to successively display information displays corresponding to at least the following:
  (i) a patient's current blood glucose level measurement as determined from a sample of the patient's blood provided on a test strip;
  (ii) an event associated with the said current blood glucose level measurement; and
  (iii) a recommended insulin dose; and
  the display screen further operative to continuously display indicia corresponding to each of the said successive information displays;
(e) at least one button that may be user-actuated operatively connected to the processor, the at least one button operative to enable a user to selectively cycle through the successive information displays on the display screen.

19. The apparatus of example 18, wherein the at least one button is a single button.

20. The apparatus of example 18, wherein the at least one button is a software programmable button located on a display screen.

21. The apparatus of examples 18, 19, or 20, wherein the continuously displayed indicia corresponding to each of the successive information displays are positioned on the display screen in an alignment with the position of the least one button.

22. The apparatus of examples 18-20, or 21, wherein the successive display on the display screen of the information display corresponding to an event associated with the said current blood glucose level measurement automatically succeeds the display of the information display corresponding to a patient's current blood glucose level measurement if the of the least one button is not user-actuated within a predetermined period of time.

23. The apparatus of examples 18-21, or 22, wherein the apparatus comprises a labeling area on which personalized identifying indicia may be provided.

24. The apparatus of examples 18-22, or 23, wherein the at least one button operatively connected to the processor is positioned adjacent the display screen.

25. The apparatus of examples 18-22, or 23, wherein the continuously displayed indicia corresponding to each of the successive information displays are positioned on the display screen in said alignment that is longitudinal with the position of the at least one button.

26. The apparatus of examples 18-23, or 24, wherein the continuously displayed indicia corresponding to each of the successive information displays are positioned on the display screen in said alignment with the position of the at least one button.

27. The apparatus of examples 18-24, or 25, wherein the continuously displayed indicia corresponding to each of the successive information displays are positioned on the display screen in an alignment that is longitudinal with the position of the at least one button.

28. The apparatus of examples 18-25, or 26, wherein the at least one button is arranged such that it is intuitive to a user that actuation of the button will effect modification in each of the associated information displays.

29. The apparatus of examples 18-27, or 28, wherein the visual alignment between the at least one button and the associated information displays results in a user-friendly and intuitive to use apparatus.

30. The apparatus of examples 18-28, or 29, wherein the display screen is divided into two distinct sections including a navigation bar section and a dynamic content section.

31. The apparatus of examples 18-29, or 30, wherein the apparatus enables at least 85% of intended users to become proficient in the primary operation of the apparatus after two test uses.

32. The apparatus of examples 18-30, or 31, wherein the apparatus is intuitive and simple to use with conspicuous features on the display screen and the apparatus enables at least 85% of intended users to become proficient in the primary operation of the apparatus after two test uses.

33. The apparatus of examples 18-31, or 32, wherein the apparatus enables at least 70%, 80%, 85%, 90%, or 95% of intended users to become proficient in the primary operation of the apparatus after one, two or three test uses.

Example 34. A method for taking blood glucose measurements and recommending insulin doses, comprising:
using an apparatus comprising:
(a) a test strip port for receiving a test strip;
(b) at least a first a computer-readable memory;
(c) a processor operatively connected to the at least first computer-readable memory;
(d) a display screen operatively connected to the processor so as to successively display information displays;
(e) at least one button that may be user-actuated operatively connected to the
processor, the at least one button operative to enable a user to selectively cycle through the successive information displays on the display screen;

obtaining a current blood glucose measurement from a blood sample and displaying that information on the display screen;

displaying an event associated with the current blood glucose level measurement; optionally confirming the accuracy of the event by actuating the at least one button; and generating a dose recommendation if required.

Example 35. A method for taking blood glucose measurements and recommending insulin doses, comprising:

using an apparatus comprising:
(a) a test strip port for receiving a test strip;
(b) at least a first a computer-readable memory;
(c) a processor operatively connected to the at least first computer-readable memory;
(d) a display screen operatively connected to the processor so as to successively display information displays information displays corresponding to at least the following:
  (i) a patient's current blood glucose level measurement as determined from a sample of the patient's blood provided on a test strip;
  (ii) an event associated with the said current blood glucose level measurement; and
  (iii) a recommended insulin dose; and
  the display screen further operative to continuously display indicia corresponding to each of the said successive information displays;
(e) at least one button that may be user-actuated operatively connected to the processor, the at least one button operative to enable a user to selectively cycle through the successive information displays on the display screen;

obtaining a blood glucose measurement from a blood sample and automatically displaying that information on the display screen;

obtaining a recommendation on whether or not insulin should be taken and automatically displaying that information on the display screen; and if insulin should be taken displaying a recommended amount of insulin.

Example 36. A method for taking blood glucose measurements and recommending insulin doses, comprising:

using an apparatus comprising:
(a) a test strip port for receiving a test strip;
(b) at least a first a computer-readable memory;
(c) a processor operatively connected to the at least first computer-readable memory;
(d) a display screen operatively connected to the processor so as to successively display information displays corresponding to at least the following:
  (i) a patient's current blood glucose level measurement as determined from a sample of the patient's blood provided on a test strip;
  (ii) an event associated with the said current blood glucose level measurement; and
  (iii) a recommended insulin dose; and
  the display screen further operative to continuously display indicia corresponding to each of the said successive information displays;
(e) a plurality of buttons that may be user-actuated operatively connected to the processor, the plurality of buttons including a first button operative to enable a user to selectively cycle through the successive information displays on the display screen, and second and third buttons operative to enable a user to selectively alter the information displayed in one or more of the successive information displays on the display screen; and wherein the continuously displayed indicia corresponding to each of the successive information displays are positioned on the display screen in an alignment with the position of the first button, and the successively displayed information is positioned on the display screen in an alignment with the second and third buttons;

obtaining a blood glucose measurement from a blood sample and automatically displaying that information on the display screen;

obtaining a recommendation on whether or not insulin should be taken and automatically displaying that information on the display screen; and if insulin should be taken displaying a recommended amount of insulin.

37. The method of example 36, wherein the display screen operatively connected to the processor so as to successively display information displays corresponding to at least the following:
  (i) a patient's current blood glucose level measurement as determined from a sample of the patient's blood provided on a test strip;
  (ii) an event associated with the said current blood glucose level measurement;
  (iii) an estimate for the number of carbohydrates associated with the said event; and
  (iv) a recommended insulin dose.

38. The method of examples 36 or 37, wherein the successive display on the display screen of the information display corresponding to an event associated with the said current blood glucose level measurement automatically succeeds the display of the information display corresponding to a patient's current blood glucose level measurement if the first button is not user-actuated within a predetermined period of time.

39. The method of examples 36, 37 or 38, wherein the apparatus is programmed to enable a user to selectively override the recommended insulin dose displayed on the display screen using one or more of the plurality of buttons.

40. The method of examples 36-38, or 39, wherein the apparatus comprises a labeling area on which personalized identifying indicia may be provided.

41. The method of examples 36-39, or 40, wherein the estimation of the number of carbohydrates associated with the said event is a measurement of the number of carbohydrates.

42. The method of examples 36-40, or 41, wherein the plurality of user-actuated buttons operatively connected to the processor are positioned adjacent the display screen.

43. The method of examples 36-41, or 42, wherein the continuously displayed indicia corresponding to each of the successive information displays are positioned on the display screen in said alignment that is longitudinal with the position of the first button.

44. The method of examples 36-42, or 43, wherein the continuously displayed indicia corresponding to each of the successive information displays are positioned on the display screen in said alignment with the position of the first button and the successively displayed information is positioned on the display screen in a longitudinal alignment with the second and third buttons.

45. The method of examples 36-43, or 44, wherein the continuously displayed indicia corresponding to each of the successive information displays are positioned on the display screen in an alignment that is longitudinal with the position of the first button and the successively displayed information is positioned on the display screen in a longitudinal alignment with the second and third buttons.

46. The method of examples 36-44, or 45, wherein the plurality of user-actuated buttons are arranged such that it is intuitive to a user that actuation of each of these buttons will effect modification in each of the associated information displays.

47. The method of examples 36-45, or 46, wherein the visual alignment between the plurality of user-actuated buttons and the associated information displays results in a process that is user-friendly and intuitive to use.

48. The apparatus of examples 36-46, or 47, wherein the display screen is divided into two distinct sections including a navigation bar section and a dynamic content section.

49. The method of examples 36-47, or 48, wherein the apparatus enables at least 85% of intended users to become proficient in the primary operation of the apparatus after two test uses.

50. The method of examples 36-48, or 49, wherein the apparatus is intuitive and simple to use with conspicuous features on the display screen and the apparatus enables at least 85% of intended users to become proficient in the primary operation of the apparatus after two test uses.

51. The method of examples 36-49, or 50, wherein the apparatus enables at least 70%, 80%, 85%, 90%, or 95% of intended users to become proficient in the primary operation of the apparatus after one, two or three test uses.

Example 52. A method for displaying a recommended insulin amount on a display screen, comprising:
using an apparatus comprising:
(a) a test strip port for receiving a test strip;
(b) at least a first a computer-readable memory;
(c) a processor operatively connected to the at least first computer-readable memory;
(d) a display screen operatively connected to the processor so as to successively display information displays;
(e) at least one button that may be user-actuated operatively connected to the processor, the at least one button operative to enable a user to selectively cycle through the successive information displays on the display screen;
obtaining a current blood glucose measurement from a blood sample and displaying that information on the display screen;
displaying an event associated with the current blood glucose level measurement; optionally confirming the accuracy of the event by actuating the at least one button; and displaying a recommended amount of insulin if required.

Example 53. A method for displaying a recommended insulin amount on a display screen, comprising:
using an apparatus comprising:
(a) a test strip port for receiving a test strip;
(b) at least a first a computer-readable memory;
(c) a processor operatively connected to the at least first computer-readable memory;
(d) a display screen operatively connected to the processor so as to successively display information displays information displays corresponding to at least the following:
(i) a patient's current blood glucose level measurement as determined from a sample of the patient's blood provided on a test strip;
(ii) an event associated with the said current blood glucose level measurement; and
(iii) a recommended insulin amount; and
the display screen further operative to continuously display indicia corresponding to each of the said successive information displays;
(e) at least one button that may be user-actuated operatively connected to the processor, the at least one button operative to enable a user to selectively cycle through the successive information displays on the display screen;
obtaining a blood glucose measurement from a blood sample and automatically displaying that information on the display screen;
obtaining a recommendation on whether or not insulin should be taken and automatically displaying that information on the display screen; and
if needed displaying a recommended amount of insulin.

Example 54. A method for displaying recommended insulin amount, comprising:
using an apparatus comprising:
(a) a test strip port for receiving a test strip;
(b) at least a first a computer-readable memory;
(c) a processor operatively connected to the at least first computer-readable memory;
(d) a display screen operatively connected to the processor so as to successively display information displays corresponding to at least the following:
(i) a patient's current blood glucose level measurement as determined from a sample of the patient's blood provided on a test strip;
(ii) an event associated with the said current blood glucose level measurement;
(iii) a determination of the number of carbohydrates associated with the said event; and
(iv) a recommended insulin amount; and the display screen further operative to continuously display indicia corresponding to each of the said successive information displays;
(e) a plurality of buttons that may be user-actuated operatively connected to the processor, the plurality of buttons including a first button operative to enable a user to selectively cycle through the successive information displays on the display screen, and second and third buttons operative to enable a user to selectively alter the information displayed in one or more of the successive information displays on the display screen; and
wherein the continuously displayed indicia corresponding to each of the successive information displays are positioned on the display screen in an alignment with the position of the first button, and the successively displayed information is positioned on the display screen in an alignment with the second and third buttons;
obtaining a blood glucose measurement from a blood sample and automatically displaying that information on the display screen;
obtaining a recommendation on whether or not insulin should be taken and automatically displaying that information on the display screen; and if needed displaying a recommended amount of insulin.

Example 55. An apparatus comprising:
(a) means for receiving a test strip;
(b) at least a first a computer-readable memory means;
(c) a processor means operatively connected to the at least first computer-readable memory;

(d) a display means operatively connected to the processor so as to successively display information displays corresponding to at least the following:
  (i) a patient's current blood glucose level measurement as determined from a sample of the patient's blood provided on a test strip;
  (ii) an event associated with the said current blood glucose level measurement; and
  (iii) a recommended insulin dose; and
  the display means further operative to continuously display indicia corresponding to each of the said successive information displays;
(e) a plurality of means that may be user-activated operatively connected to the processor, the plurality of means including a first means operative to enable a user to selectively cycle through the successive information displays on the display means, and second and third means operative to enable a user to selectively alter the information displayed in one or more of the successive information displays on the display means; and
wherein the continuously displayed indicia corresponding to each of the successive information displays are positioned on the display means in an alignment with the position of the first means, and the successively displayed information is positioned on the display means in an alignment with the second and third means.

56. The apparatus of example 55, wherein the display means operatively connected to the processor means so as to successively display information displays corresponding to at least the following:
  (i) a patient's current blood glucose level measurement as determined from a sample of the patient's blood provided on a test strip;
  (ii) an event associated with the said current blood glucose level measurement;
  (iii) an estimate for the number of carbohydrates associated with the said event; and (iv) a recommended insulin dose.

57. The apparatus of examples 55 or 56, wherein the successive display on the display means of the information display corresponding to an event associated with the said current blood glucose level measurement automatically succeeds the display of the information display corresponding to a patient's current blood glucose level measurement if the first means is not user-actuated within a predetermined period of time.

58. The apparatus of examples 55, 56, or 57, wherein the apparatus is programmed to enable a user to selectively override the recommended insulin dose displayed on the display means using one or more of the plurality of buttons.

59. The apparatus of examples 55-57, or 58, wherein the apparatus comprises a labeling area on which personalized identifying indicia may be provided.

60. The apparatus of examples 55-58, or 59, wherein the estimation of the number of carbohydrates associated with the said event is a measurement of the number of carbohydrates.

61. The apparatus of examples 55-59, or 60, wherein the plurality of means that may be user-actuated operatively connected to the processor are positioned adjacent the display means.

62. The apparatus of examples 55-60, or 61, wherein the continuously displayed indicia corresponding to each of the successive information displays are positioned on the display means in said alignment that is longitudinal with the position of the first means.

63. The apparatus of examples 55-61, or 62, wherein the continuously displayed indicia corresponding to each of the successive information displays are positioned on the display means in said alignment with the position of the first means and the successively displayed information is positioned on the display screen in a longitudinal alignment with the second and third means.

64. The apparatus of examples 55-62, or 63, wherein the continuously displayed indicia corresponding to each of the successive information displays are positioned on the display means in an alignment that is longitudinal with the position of the first means. and the successively displayed information is positioned on the display screen in a longitudinal alignment with the second and third means.

65. The apparatus of examples 55-63, or 64, wherein the plurality of user-actuated means are arranged such that it is intuitive to a user that actuation of each of these means will effect modification in each of the associated information displays.

66. The apparatus of examples 55-64, or 65, that is user-friendly and intuitive to use.

67. The apparatus of examples 55-65, or 66, wherein the visual alignment between the plurality of user-actuated buttons and the associated information displays results in a user-friendly and intuitive to use apparatus.

68. The apparatus of examples 55-66, or 67, wherein the display means is divided into two distinct sections including a navigation bar section and a dynamic content section.

69. The apparatus of examples 55-67, or 68, wherein the at least one of the means that may be user-actuated is a software programmable button located on a display means.

70. The apparatus of examples 55-68, or 69, wherein the apparatus enables at least 85% of intended users to become proficient in the primary operation of the apparatus after two test uses.

71. The apparatus of examples 55-69, or 70, wherein the apparatus is intuitive and simple to use with conspicuous features on the display screen and the apparatus enables at least 85% of intended users to become proficient in the primary operation of the apparatus after two test uses.

72. The apparatus of examples 55-70, or 71, wherein the apparatus enables at least 70%, 80%, 85%, 90%, or 95% of intended users to become proficient in the primary operation of the apparatus after one, two or three test uses.

Example 73. An apparatus comprising:
(a) means for receiving a test strip;
(b) at least a first a computer-readable memory means;
(c) a processor means operatively connected to the at least first computer-readable memory;
(d) a display means operatively connected to the processor so as to successively display information displays corresponding to at least the following:
  (i) a patient's current blood glucose level measurement as determined from a sample of the patient's blood provided on a test strip;
  (ii) an event associated with the said current blood glucose level measurement; and
  (iii) a recommended insulin dose; and
  the display means further operative to continuously display indicia corresponding to each of the said successive information displays;
(e) at least one means that may be user-actuated operatively connected to the processor, the at least one means operative to enable a user to selectively cycle through the successive information displays on the display means.

74. The apparatus of example 73, wherein the at least one means is a single button.

75. The apparatus of examples claim 73 or 74, wherein the at least one means is a software programmable means located on a display means.

76. The apparatus of examples 73, 74 or 75, wherein the continuously displayed indicia corresponding to each of the successive information displays are positioned on the display means in an alignment with the position of the least one means.

77. The apparatus of examples 73-75, or 76, wherein the successive display on the display means of the information display corresponding to an event associated with the said current blood glucose level measurement automatically succeeds the display of the information display corresponding to a patient's current blood glucose level measurement if the of the least one means is not user-actuated within a predetermined period of time.

78. The apparatus of examples 73-76, or 77, wherein the apparatus is programmed to enable a user to selectively override the recommended insulin dose displayed on the display means using the at least one means.

79. The apparatus of examples 73-77, or 78, wherein the apparatus comprises a labeling area on which personalized identifying indicia may be provided.

80. The apparatus of examples 73-78, or 79, wherein the at least one means operatively connected to the processor is positioned adjacent the display means.

81. The apparatus of examples 73-79, or 80, wherein the continuously displayed indicia corresponding to each of the successive information displays are positioned on the display means in said alignment that is longitudinal with the position of the at least one means.

82. The apparatus of examples 73-80 or 81, wherein the continuously displayed indicia corresponding to each of the successive information displays are positioned on the display means in said alignment with the position of the at least one means.

83. The apparatus of examples 73-81, or 82, wherein the continuously displayed indicia corresponding to each of the successive information displays are positioned on the display means in an alignment that is longitudinal with the position of the at least one means.

84. The apparatus of examples 73-82, or 83, wherein the at least one means is arranged such that it is intuitive to a user that actuation of the means will effect modification in each of the associated information displays.

85. The apparatus of examples 73-83, or 84, wherein the visual alignment between the at least one means and the associated information displays results in a user-friendly and intuitive to use apparatus.

86. The apparatus of examples 73-84, or 85, wherein the display means is divided into two distinct sections including a navigation bar section and a dynamic content section.

87. The apparatus of examples 73-85, or 86, wherein the apparatus enables at least 85% of intended users to become proficient in the primary operation of the apparatus after two test uses.

88. The apparatus of examples 73-86, or 87, wherein the apparatus is intuitive and simple to use with conspicuous features on the display means and the apparatus enables at least 85% of intended users to become proficient in the primary operation of the apparatus after two test uses.

89. The apparatus of examples 73-87, or 88, wherein the apparatus enables at least 70%, 80%, 85%, 90%, or 95% of intended users to become proficient in the primary operation of the apparatus after one, two or three test uses.

Example 90. An apparatus for taking blood glucose measurements and recommending insulin doses, comprising:
a body for housing:
  (a) a test strip port for receiving a test strip;
  (b) at least a first a computer-readable memory;
  (c) a processor operatively connected to the at least first computer-readable memory; (d) a display screen operatively connected to the processor so as to successively display information displays corresponding to at least the following:
    (i) a patient's current blood glucose level measurement as determined from a sample of the patient's blood provided on a test strip;
    (ii) an event associated with the said current blood glucose level measurement;
    (iii) a measurement for the number of carbohydrates associated with the said event; and
    (iv) a recommended insulin dose; and
  the display screen further operative to continuously display indicia corresponding to each of the said successive information displays;
  (e) a plurality of user-actuated buttons operatively connected to the processor and positioned adjacent the display screen, the plurality of buttons including a first button operative to enable a user to selectively cycle through the successive information displays on the display screen, and second and third buttons operative to enable a user to selectively alter the information displayed in one or more of the successive information displays on the display screen; and
  wherein the continuously displayed indicia corresponding to each of the successive information displays are positioned on the display screen in longitudinal alignment with the position of the first button, and the successively displayed information is positioned on the display screen in alignment with the second and third buttons.

91. The apparatus of example 90, wherein the successive display on the display screen of the information display corresponding to an event associated with the said current blood glucose level measurement automatically succeeds the display of the information display corresponding to a patient's current blood glucose level measurement if the first button is not user-actuated within a predetermined period of time.

92. The apparatus of examples 90 or 91, wherein the apparatus is programmed to enable a user to selectively override the recommended insulin dose displayed on the display screen using one or more of the plurality of buttons.

93. The apparatus of examples 90, 91 or 92, wherein the apparatus comprises a labeling area on which a user may provide personalized identifying indicia.

It will be appreciated that the apparatus of the present disclosure provides an intuitive user interface facilitating data entry by a user, as well as, optionally, programming permitting the user to override an insulin dose recommendation provided by the apparatus.

The foregoing description of certain exemplary embodiments has been presented for purposes of illustration and description. It is not intended to be exhaustive of, or to limit, the disclosure to the precise form disclosed, and modification and variations are possible in light of the teachings herein or may be acquired from practice of the disclosed embodiments. The embodiments shown and described in order to explain the principles of the inventions and its practical application to enable one skilled in the art to utilize various embodiments and with various modifications as are suited to the particular application contemplated. Accordingly, such modifications and embodiments are intended to be included within the scope of the disclosure. Other substitutions, modifications, changes and omissions may be made in the design, operating conditions, and arrangement of the exemplary embodiment without departing from the spirit of the present disclosure.

The invention claimed is:

1. An apparatus comprising:
   (a) a test strip port for receiving a test strip;
   (b) at least a first non-transitory computer-readable medium;
   (c) a processor operatively connected to the at least first non-transitory computer-readable medium, the processor programmed at least to automatically combine multiple data inputs via an algorithm to determine a recommended number of insulin units;
   (d) a touch screen that comprises a display screen operatively connected to the processor and the processor is programmed to cause the display to successively display information corresponding to at least the following:
      (i) a patient's current blood glucose level measurement as determined from a sample of the patient's blood provided on a test strip;
      (ii) an event associated with the said current blood glucose level measurement; and
      (iii) a recommended number of insulin units; and the processor is further programmed to cause the display screen to continuously display indicia corresponding to each of the said successive information displays;
   (e) a plurality of buttons that are software programmable buttons located on the touch screen and are user-activated operatively connected to the processor, the plurality of buttons including a at least a first button, a second button and a third button, and the processor is further programmed enable a user to selectively cycle through the successive information displays on the display screen when the first button is pressed, and enable a user to selectively alter the information displayed in one or more of the successive information displays on the display screen when the second and third buttons are pressed; and
   wherein the continuously displayed indicia corresponding to each of the successive information displays are positioned on the display screen in a linear alignment with the position of the first button, and the successively displayed information is positioned on the display screen in a linear alignment with the second and third buttons.

2. The apparatus of claim 1, wherein the display screen operatively connected to the processor so as to successively display information displays corresponding to at least the following:
   (i) a patient's current blood glucose level measurement as determined from a sample of the patient's blood provided on a test strip;
   (ii) an event associated with the said current blood glucose level measurement;
   (iii) an estimate for the number of incoming carbohydrates associated with the said event; and
   (iv) a recommended insulin dose; and
   wherein the estimate for the number of incoming carbohydrates factors into a calculation to determine the recommended insulin dose.

3. The apparatus of claim 1, wherein the successive display on the display screen of the information display corresponding to an event associated with the said current blood glucose level measurement automatically transitions from the display of the information display corresponding to a patient's current blood glucose level measurement if the first button is not user-actuated within a predetermined period of time.

4. The apparatus of claim 1, wherein the apparatus is programmed to enable a user to selectively override the recommended insulin dose displayed on the display screen using one or more of the plurality of buttons.

5. The apparatus of claim 1, wherein the apparatus comprises a labeling area on which personalized identifying indicia may be provided.

6. The apparatus of claim 1, wherein the estimation of the number of carbohydrates associated with the said event is a measurement of the number of carbohydrates.

7. The apparatus of claim 1, wherein the continuously displayed indicia corresponding to each of the successive information displays are positioned on the display screen in said alignment that is longitudinal with the position of the first button.

8. The apparatus of claim 1, wherein the continuously displayed indicia corresponding to each of the successive information displays are positioned on the display screen in said alignment with the position of the first button and the successively displayed information is positioned on the display screen in a longitudinal alignment with the second and third buttons.

9. The apparatus of claim 1, wherein the continuously displayed indicia corresponding to each of the successive information displays are positioned on the display screen in an alignment that is longitudinal with the position of the first button and the successively displayed information is positioned on the display screen in a longitudinal alignment with the second and third buttons.

10. The apparatus of claim 1, wherein the display screen is divided into two distinct sections including a navigation bar section and a dynamic content section.

11. The apparatus of claim 1, wherein the removal of any redundant functionality enables at least 85% of intended users to perform the primary operation of the apparatus after two test uses.

12. The apparatus of claim 1, wherein conspicuous features on the display screen and the apparatus enables at least 85% of intended users to perform the primary operation of the apparatus after two test uses.

13. The apparatus of claim 1, wherein the apparatus simplifies the user experience so as to enables at least 70%, 80%, 85%, 90%, or 95% of intended users to perform the primary operation of the apparatus after one, two or three test uses.

14. An apparatus comprising:
   (a) a test strip port for receiving a test strip;
   (b) at least a first non-transitory computer-readable medium;
   (c) a processor operatively connected to the at least first non-transitory computer-readable medium, the processor programmed at least to automatically combine multiple data inputs via an algorithm to determine a recommended number of insulin units
   (d) a touch screen that comprises a display screen operatively connected to the processor and the processor is programmed to cause the display to successively display information corresponding to at least the following:

(i) a patient's current blood glucose level measurement as determined from a sample of the patient's blood provided on a test strip;
(ii) an event associated with the said current blood glucose level measurement; and
(iii) a recommended number of insulin units; and the processor is further programmed to cause the display screen to continuously display indicia corresponding to each of the said successive information displays;

(e) at least one button that is a software programmable button located on the touch screen and is user-actuated operatively connected to the processor, and the processor is further programmed to enable a user to selectively cycle through the successive information displays on the display screen when the at least one button is pressed.

15. The apparatus of claim 14, wherein the at least one button is a single button.

16. The apparatus of claim 14, wherein the apparatus is programmed to support at least three insulin regimens: 1) basal only; 2) premixed; and 3) basal-bolus that does not require carbohydrate counting.

\* \* \* \* \*